United States Patent
Freyne et al.

(10) Patent No.: US 6,656,959 B1
(45) Date of Patent: Dec. 2, 2003

(54) PDE IV INHIBITING PYRIDINE DERIVATIVES

(75) Inventors: Eddy Jean Freyne, Rumst (BE); Gaston Stanislas Diels, Ravels (BE); Maria Encarnacion Matesanz-Ballesteros, Toledo (ES); Adolfo Diaz-Martinez, Madrid (ES)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 09/647,668

(22) PCT Filed: Mar. 24, 1999

(86) PCT No.: PCT/EP99/02045

§ 371 (c)(1),
(2), (4) Date: Sep. 29, 2000

(87) PCT Pub. No.: WO99/50262

PCT Pub. Date: Oct. 7, 1999

(51) Int. Cl.[7] .................. A61K 31/44; A61K 31/535; A61K 31/495; C07D 413/00; C07D 401/00

(52) U.S. Cl. ............... 514/336; 514/332; 514/235.5; 514/253.01; 544/124; 544/360; 546/194; 546/256; 546/193

(58) Field of Search .............. 546/274.1, 256, 546/194, 193; 514/341, 235.5, 253.01, 332, 336; 544/124, 360

(56) References Cited

U.S. PATENT DOCUMENTS

| 3,876,657 A | * | 4/1975 | Aelony et al. | |
|---|---|---|---|---|
| 4,600,430 A | | 7/1986 | Abdulla et al. | ............... 71/92 |

FOREIGN PATENT DOCUMENTS

| HU | 196 890 B | 2/1985 |
|---|---|---|
| WO | WO 95/04045 | 2/1995 |
| WO | WO 96/31485 | 10/1996 |
| WO | WO 96/31486 | 10/1996 |
| WO | WO 96/31487 | 10/1996 |
| WO | WO 97/03967 | 2/1997 |
| WO | WO 9724122 | * 10/1997 |
| WO | WO 98/14432 | 4/1998 |

OTHER PUBLICATIONS

Burger, A. (Ed.), "Bioisosterism in molecular modification," *Medicinal Chemistry*, 3rd Ed., *Wiley–Interscience Division of John Wiley & Sons*, 1970, Part 1, 72–80.

King, F.D. (Ed.), "Bioisosteres, conformational restriction and pro–drugs—case history: an example of a conformational restriction approach," *Medical Chemistry: Principles and Practice*, 1994, Chapter 14, 206–209.

Thomber, C.W., "Isosterism and molecular modification in drug design," *Chem. Soc. Rev.*, 1979, 8, 563–580.

* cited by examiner

*Primary Examiner*—Alan L. Rotman
*Assistant Examiner*—Binta Robinson
(74) *Attorney, Agent, or Firm*—Woodcock Washburn LLP

(57) ABSTRACT

The present invention concerns pyridine derivatives having the formula

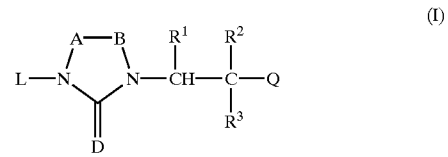

the N-oxide forms, the pharmaceutically acceptable addition salts and the stereochemically isomeric forms thereof, wherein L is hydrogen; $C_{1-6}$alkyl; $C_{1-6}$alkyl carbonyl; $C_{1-6}$alkyloxycarbonyl; substituted $C_{1-6}$alkyl; $C_{3-6}$alkenyl; substituted $C_{3-6}$alkenyl; piperidyl; substituted piperidyl; $C_{1-6}$alkylsulfonyl or arylsulfonyl; —A—B— is —$CR^8$=$CR^5$— or —$CHR^4$—$CHR^5$—; D is O or $NR^6$; $R^1$ is a hydrogen or $C_{1-4}$alkyl; $R^2$ is hydrogen; halo; $C_{1-6}$alkyl; trifluoromethyl; $C_{3-6}$cycloalkyl; carboxyl; $C_{1-4}$alkyl oxycarbonyl; $C_{3-6}$cycloalkylaminocarbonyl; aryl; $Het^1$; or substituted $C_{1-6}$alkyl; or $R^2$ is —O—$R^9$ or —NH—$R^{10}$; $R^3$ is hydrogen, halo, hydroxy, $C_{1-6}$alkyl or $C_{1-6}$alkyloxy; or $R^2$ and $R^1$, or $R^2$ and $R^3$ taken together may form a bivalent radical; Q is disubstituted pyridine; $R^7$ and $R^8$ each independently are hydrogen; $C_{1-6}$alkyl; difluoromethyl; trifluoromethyl; $C_{3-6}$cyclo alkyl; a saturated 5-, 6- or 7-membered heterocycle containing one or two heteroatoms selected from oxygen, sulfur or nitrogen; indanyl; 6,7-dihydro-5H-cyclopentapyridyl; bicyclo[2.2.1]-2-heptenyl; bicyclo[2.2.1]heptanyl; $C_{1-6}$alkylsulfonyl; arylsulfonyl; or substituted $C_{1-10}$alkyl; having PDE IV and cytokine inhibiting activity. The invention also relates to processes for preparing the compounds of formula (I), pharmaceutical compositions thereof and their use as a medicament.

10 Claims, No Drawings

PDE IV INHIBITING PYRIDINE DERIVATIVES

This application is a National Stage application under 35 U.S.C. §371 of PCT/EP99/02045 filed Mar. 24, 1999, which claims priority from EP 98.201.020.9, filed Apr. 1, 1998.

The present invention concerns pyridine derivatives having phosphodiesterase IV (PDE IV) and cytokine inhibiting activity and their preparation; it further relates to compositions comprising them, as well as their use as a medicine.

WO95/04045 generically discloses 2-pyridinyl-1-[dialkyloxypiridinyl]-ethanone derivates useful for treating phosphodiesterase IV related disorders. WO 96/31485 describes a number of 1,3-dihydro-1-(phenylalkyl)-2H-imidazol-2-one derivatives having PDE IV and cytokine inhibiting activity.

The compounds of the present invention are structurally different from art-known PDE IV inhibitors. They have therapeutical utility in the treatment of disease states related to an abnormal enzymatic or catalytic activity of PDE IV, and/or disease states related to a physiologically detrimental excess of cytokines, in particular allergic, atopic and inflammatory diseases. The present compounds have an improved pharmacological profile with little or no gastro-intestinal side-effects, which are often associated with art-known PDE IV inhibitors.

The present invention concerns pyridine derivatives having the formula

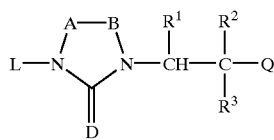
(I)

wherein:

L is hydrogen; $C_{1-6}$alkyl; $C_{1-6}$alkyl substituted with one or two substituents selected from the group consisting of hydroxy, $C_{1-4}$alkyloxy, $C_{1-4}$alkyloxycarbonyl, mono- and di($C_{1-4}$alkyl)amino, aryl and Het$^2$; $C_{3-6}$alkenyl; $C_{3-6}$alkenyl substituted with aryl; $C_{1-6}$alkylcarbonyl; $C_{1-6}$alkyloxycarbonyl; piperidyl; piperidyl substituted with $C_{1-4}$alkyl or aryl$C_{1-4}$alkyl; $C_{1-6}$alkylsulfonyl or arylsulfonyl;

—A—B— is a bivalent radical of formula:

| —CR$^4$=CR$^5$—; | (a-1) |
|---|---|
| or | |
| —CHR$^4$—CHR$^5$—; | (a-2) |

D is O or NR$^6$;
Q is a radical of the formula

(b-1)

(b-2)

(b-3)

$R^1$ is hydrogen or $C_{1-4}$alkyl;
or $R^1$ and $R^2$ together may form a bivalent radical of formula —(CH$_2$)$_m$— wherein m is 1, 2, 3 or 4;
$R^2$ is hydrogen; halo; $C_{1-6}$alkyl; trifluoromethyl; $C_{3-6}$cycloalkyl; carboxyl; $C_{1-4}$alkyloxycarbonyl; $C_{3-6}$cycloalkylaminocarbonyl; aryl; Het$^1$; or $C_{1-6}$alkyl substituted with cyano, amino, hydroxy, $C_{1-4}$alkylcarbonylamino, aryl or Het$^1$; or
$R^2$ is a radical of formula:
—O—R$^9$ (c-1); or
—NH—R$^{10}$ (c-2);
$R^3$ is hydrogen, halo, hydroxy, $C_{1-6}$alkyl or $C_{1-6}$alkyloxy; or
$R^2$ and $R^3$ taken together may form a bivalent radical of formula:

| —(CH$_2$)$_n$—; | (d-1) |
|---|---|
| —CH$_2$—CH$_2$—O—CH$_2$—CH$_2$—; | (d-2) |
| —CH$_2$—CH$_2$—N(R$^{11}$)—CH$_2$—CH$_2$—; | (d-3) |
| or | |
| —CH$_2$—CH=CH—CH$_2$—; | (d-4) | wherein n is 2, 3, 4 or 5;
$R^4$ and $R^5$ are each independently selected from hydrogen or $C_{1-4}$alkyl;
$R^6$ is hydrogen, $C_{1-4}$alkyl or cyano;
$R^7$ and $R^8$ each independently are hydrogen; $C_{1-6}$alkyl; difluoromethyl; trifluoromethyl; $C_{3-6}$cycloalkyl; a saturated 5-, 6- or 7-membered heterocycle containing one or two heteroatoms each independently selected from oxygen, sulfur or nitrogen; indanyl; 6,7-dihydro-5H-cyclopentapyridyl; bicyclo[2.2.1]-2-heptenyl; bicyclo[2.2.1]heptanyl; $C_{1-6}$alkylsulfonyl; arylsulfonyl; or $C_{1-6}$alkyl substituted with one or two substituents each independently selected from aryl, pyridyl, thienyl, furanyl, indanyl, 6,7-dihydro-5H-cyclopentapyridyl, $C_{3-7}$cycloalkyl and a saturated 5-, 6- or 7-membered heterocycle containing one or two heteroatoms selected from oxygen, sulfur or nitrogen;
$R^9$ is hydrogen; $C_{1-6}$alkyl; $C_{1-6}$alkyl substituted with hydroxy, carboxyl, $C_{1-4}$alkyloxycarbonyl, amino, mono- or di($C_{1-4}$alkyl)amino, Het$^1$ or aryl;
$R^{10}$ is hydrogen; $C_{1-6}$alkyl; $C_{1-4}$alkylcarbonyl; $C_{1-6}$alkyl substituted with hydroxy, carboxyl, $C_{1-4}$alkyloxycarbonyl, amino, mono- or di($C_{1-4}$alkyl)amino, Het$^1$ or aryl;
$R^{11}$ is hydrogen, $C_{1-6}$alkyl, $C_{1-6}$alkylsulfonyl or p-toluenesulfonyl;
aryl is phenyl or phenyl substituted with one, two or three substituents each independently selected from halo, hydroxy, $C_{1-4}$alkyl, $C_{1-4}$alkyloxy, $C_{3-6}$cycloalkyl, trifluoromethyl, amino, nitro, carboxyl, $C_{1-4}$alkyloxycarbonyl and $C_{1-4}$alkylcarbonylamino;
Het$^1$ is pyridyl; pyridyl substituted with $C_{1-4}$alkyl; furanyl; furanyl substituted with $C_{1-4}$alkyl; thienyl; thienyl substituted with $C_{1-4}$alkylcarbonylamino; hydroxypyridyl, hydroxypyridyl substituted with $C_{1-4}$alkyl or $C_{1-4}$alkoxy$C_{1-4}$alkyl; imidazolyl; imidazolyl substituted with $C_{1-4}$alkyl; thiazolyl; thiazolyl substituted with $C_{1-4}$alkyl; oxazolyl; oxazolyl substituted with $C_{1-4}$alkyl;

isoquinolinyl; isoquinolinyl substituted with $C_{1-4}$alkyl; quinolinonyl; quinolinonyl substituted with $C_{1-4}$alkyl; morpholinyl; piperidyl; piperidyl substituted with $C_{1-4}$alkyl, $C_{1-4}$alkyloxycarbonyl or aryl$C_{1-4}$alkyl; piperazinyl; piperazinyl substituted with $C_{1-4}$alkyl, $C_{1-4}$alkyloxycarbonyl or aryl$C_{1-4}$alkyl; and Het² is morpholinyl; piperidyl; piperidyl substituted with $C_{1-4}$alkyl or aryl$C_{1-4}$alkyl; piperazinyl; piperazinyl substituted with $C_{1-4}$alkyl or aryl$C_{1-4}$alkyl; pyridyl; pyridyl substituted with $C_{1-4}$alkyl; furanyl; furanyl substituted with $C_{1-4}$alkyl; thienyl or thienyl substituted with $C_{1-4}$alkyl or $C_{1-4}$alkylcarbonylamino;

the N-oxide forms, the pharmaceutically acceptable acid or base addition salts and the stereochemically isomeric forms thereof.

Some of the compounds of formula (I) may also exist in their tautomeric forms. Such forms although not explicitly indicated in the above formula are intended to be included within the scope of the present invention. In particular, compounds of formula (I) wherein L is hydrogen may exist in their corresponding tautomeric form.

In $R^7$ and $R^8$, the saturated 5-, 6- or 7-membered heterocycles containing one or two heteroatoms selected from oxygen, sulfur or nitrogen may suitably be selected from heterocycles such as, for example, tetrahydrofuranyl, dioxolanyl, pyrrolidinyl, morpholinyl, piperidyl, piperazinyl and tetrahydropyranyl. Said heterocyclic radicals are attached to the oxygen atom or the $C_{1-10}$alkyl radical by any carbon atom or, where appropriate, by a nitrogen atom.

Also in $R^7$ and $R^8$, the term 6,7-dihydro-5H-cyclopentapyridyl is meant to represent 6,7hydro-5H-cyclopenta[b]pyridyl or 6,7-dihydro-5H-cyclopenta[c]pyridyl and may be attached to the remainder of the molecule by any of the aliphatic or aromatic carbon atoms.

As used herein the term halo is generic to fluoro, chloro, bromo and iodo; the term $C_{1-4}$alkyl is meant to include straight chained or branched saturated hydrocarbons having from 1 to 4 carbon atoms such as, for example, methyl, ethyl, 1-methylethyl, 1,1dimethylethyl, propyl, 2-methylpropyl and butyl; the term $C_{1-6}$alkyl is meant to include $C_{1-4}$alkyl and the higher homologues thereof having 5 or 6 carbon atoms such as, for example, 2-methylbutyl, pentyl, hexyl and the like; the term $C_{10}$alkyl is meant to include $C_{1-6}$alkyl and the higher homologues thereof having from 7 to 10 carbon atoms such as, for example, heptyl, octyl, nonyl, decyl, I -methylhexyl, 2-methylheptyl and the like; the term $C_{3-6}$alkenyl defines straight and branch chained hydrocarbon radicals containing one double bond and having from 3 to 6 carbon atoms such as, for example, 2-propenyl, 3-butenyl, 2-butenyl, 2-pentenyl, 3-pentenyl, 3-methyl-2-butenyl and the like; and the carbon atom of said $C_{3-6}$alkenyl being connected to a nitrogen atom preferably is saturated; the term $C_{3-6}$cycloalkyl is generic to cyclopropyl, cyclobutyl, cyclopentyl and cyclohexyl; the term $C_{3-7}$cycloalkyl is meant to include $C_{3-6}$cycloalkyl and cycloheptyl; the term $C_{1-4}$alkanediyl is meant to include straight chained and branched saturated bivalent hydrocarbon radicals having from 1 to 4 carbon atoms, such as, for example, methylene, 1,2-ethanediyl, 1,1-ethanediyl, 1,3-propanediyl, 1,2-propanediyl, 1,4-butanediyl, 2-methyl-1,3-propanediyl and the like.

As used in the foregoing definitions and hereinafter, halo$C_{1-4}$alkanediyl is defined as mono- or polyhalosubstituted $C_{1-4}$alkanediyl, in particular $C_{1-4}$alkanediyl substituted with one or more fluoro atoms.

The pharmaceutically acceptable acid addition salts as mentioned hereinabove are meant to comprise the acid addition salt forms which can conveniently be obtained by treating the base form of the compounds of formula (I) with appropriate acids such as inorganic acids, for example, hydrohalic acid, e.g. hydrochloric or hydrobromic, sulfuric, nitric, phosphoric and the like acids; or organic acids, such as, for example, acetic, hydroxy-acetic, propanoic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely, said acid addition salt forms can be converted in the free base forms by treatment with an appropriate base.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt also comprises the hydrates and solvent addition forms which the compounds of formula (I) are able to form. Examples of such forms are e.g. hydrates, alcoholates and the like.

The N-oxide forms of the compounds of formula (I) are meant to comprise those compounds of formula (I) wherein one or several nitrogen atoms are oxidized to the so-called N-oxide.

The term "stereochemically isomeric forms" as used hereinbefore defines all the possible stereoisomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration, and the =$NR^6$ and substituted $C_{3-6}$alkenyl moieties may have the E- or Z-configuration.

Whenever used hereinafter, the term compounds of formula (I) is meant to include also the N-oxide forms, the pharmaceutically acceptable acid or base addition salts and all stereoisomeric forms.

A special group of compounds includes those compounds of formula (I) wherein $R^7$ and $R^8$ each independently are hydrogen; $C_{1-6}$alkyl; $C_{3-6}$cycloalkyl; difluoromethyl; trifluoromethyl; a saturated 5-, 6- or 7-membered heterocycle containing one or two heteroatoms selected from oxygen, sulfur or nitrogen; indanyl; bicyclo[2.2.1]-2-heptenyl; bicyclo[2.2.1]heptanyl; $C_{1-6}$alkylsulfonyl; arylsulfonyl; or $C_{1-10}$alkyl substituted with one or two substituents each independently selected from aryl, pyridyl, thienyl, furanyl, $C_{3-7}$cycloalkyl and a saturated 5-, 6- or 7-membered heterocycle containing one or two heteroatoms selected from oxygen, sulfur or nitrogen.

Interesting compounds are those compounds of formula (I) wherein $R^2$ and $R^3$ are each independently $C_{1-6}$alkyl; $C_{3-6}$cycloalkyl; difluoromethyl; a saturated 5-, 6- or 7-membered heterocycle containing one or two heteroatoms selected from oxygen, sulfur or nitrogen; indanyl; or $C_{1-10}$alkyl substituted with aryl, indanyl, 6,7-dihydro-5H-cyclopentapyridyl or $C_{3-6}$cycloalkyl.

Also interesting compounds are those compounds of formula (I) wherein $R^2$ and $R^3$ are each independently hydrogen, hydroxy or $C_{1-6}$alkyl.

Particular compounds are those compounds of formula (I) wherein $R^7$ is cyclopentyl, tetrahydrofuranyl, cyclopropylmethyl, 5-phenylpentyl or indanyl; $R^8$ is hydrogen, methyl or difluoromethyl; $R^2$ is hydrogen or methyl; $R^3$ is hydrogen, hydroxy or methyl and $R^1$, $R^4$, $R^5$ and L are hydrogen.

Most preferred are the following compounds: [1-[2-[6-(cyclopentyloxy)-5-methoxy-2-pyridinyl]propyl]-1,3-dihydro-2H-imidazol-2-ylidene]cyanamide; and [1-[2-[6-(cyclopentyloxy)-5-methoxy-2-pyridinyl]propyl]-1,3-dihydro-2H-imidazol-2-one, their N-oxides, their stereochemically isomeric forms and their pharmaceutically acceptable addition salts.

Whenever used hereinafter, $R^1$ to $R^{11}$, L, D, Q and —A—B— are defined as under formula (I) unless otherwise indicated.

Compounds of formula (I) wherein —A—B— is a radical of formula (a-1) and L is hydrogen, said compounds being represented by formula (I-a-1), can conveniently be prepared by cyclization of an intermediate of formula (II) or a functional derivative thereof in the presence of a suitable acid such as, for example, hydrochloric acid.

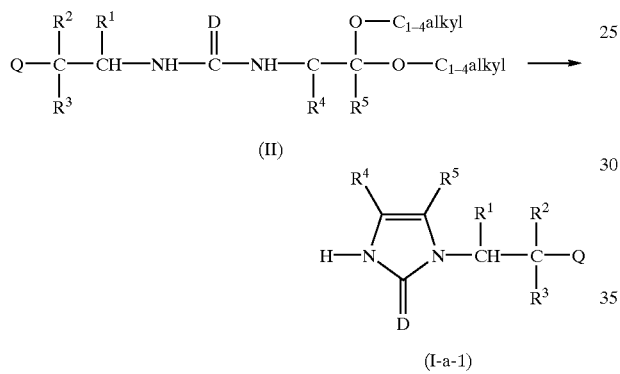

Said cyclization may be performed in a reaction inert solvent such as, for example, tetrahydrofuran, 1,4-dioxane or a mixture thereof. Stirring and heating may enhance the rate of the reaction.

In this and the following preparations, the reaction products may be isolated from the reaction medium and, if necessary, further purified according to methodologies generally known in the art such as, for example, extraction, crystallization, trituration and chromatography.

In particular, compounds of formula (I-a-1) wherein $R^2$ is hydroxy, said compounds being represented by formula (I-a-1-1), may be prepared by cyclization of an intermediate of formula (II-1) wherein P is hydrogen or, preferably, is a trimethylsilyl protecting group or a functional derivative thereof, in a manner analogous to the one described for the preparation of a compound of formula (I-a-1) from an intermediate of formula (II).

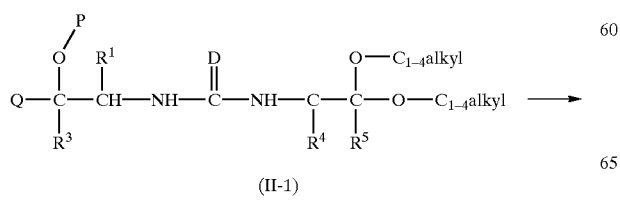

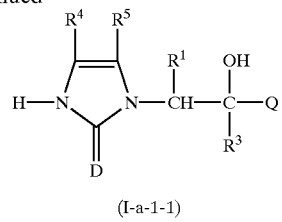

The compounds of formula (I) can also be converted into each other following art-known procedures of functional group transformation.

For example, compounds of formula (I) wherein L is other than hydrogen, said compounds being represented by formula (I-b), may be prepared by reacting a compound of formula (I-a) with L'-W² (III), wherein L' is the same as L defined under formula (I) but other than hydrogen and W² is a reactive leaving group such as, for example, a halogen atom.

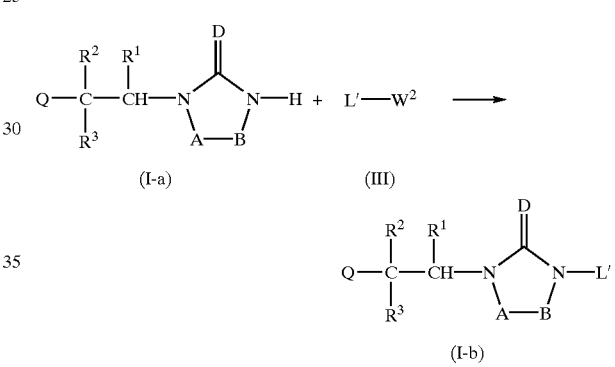

Also art-known addition reactions may be used to convert compounds of formula (I-a) into compounds of formula (I-b).

Compounds of formula (I-a) wherein —A—B— is a radical of formula (a-2), said compounds being represented by formula (I-a-2), can be prepared by hydrogenation of compounds of formula (I-a) wherein —A—B— is a radical of formula (a-1), said compounds being represented by formula (I-a-1), using art-known hydrogenation techniques. For instance, hydrogen in the presence of a suitable catalyst such as, for example, palladium or platinum supported on for instance charcoal may be used as an appropriate hydrogenation agent.

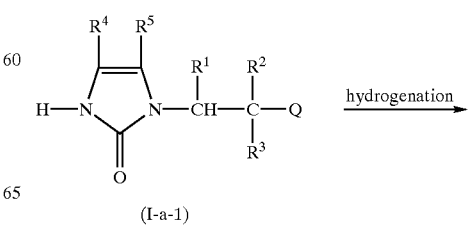

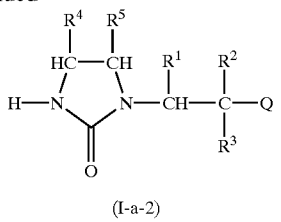

(I-a-2)

Compounds of formula (I) wherein $R^2$ is hydroxy and $R^3$ is methyl, said compounds being represented by formula (I-a-1-2), may be prepared by oxidizing a compound of formula (I) wherein $R^2$ is hydroxy and $R^3$ is hydrogen, said compounds being represented by formula (I-a-1-3) with a suitable oxidizing agent, such as, for example, ethanediol dichloride, in a suitable reaction inert solvent, such as, for example, dichloromethane, in the presence of a suitable base, such as, for example, triethylamine, followed by reacting the thus formed intermediate with a Grignard reagent.

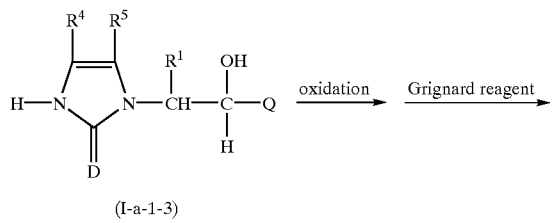

(I-a-1-3)

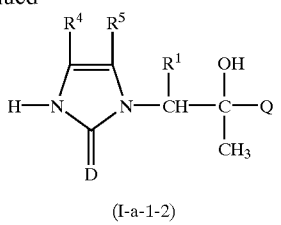

(I-a-1-2)

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with 3-phenyl-2-(phenylsulfonyl)oxaziridine or with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

Intermediates mentioned hereinabove may be prepared following art-known techniques.

In particular, intermediates of formula (II) wherein D is N—CN, said compounds being represented by formula (II-a) may be prepared by first reacting an amine of formula (IV) with dimethyl cyanocarbonimidodithioate or diphenyl cyanocarbonimidate or a functional derivative thereof. Said reaction can conveniently be performed in a reaction inert solvent such as, for example, dichloromethane, benzene or toluene, optionally cooled on an ice-bath, and in the presence of a base such as, for example, triethylamine or sodiumbicarbonate. The thus obtained intermediate may be subsequently reacted with an intermediate of formula (V) or a functional derivative thereof, to form an intermediate of formula (II-a). Said reaction can conveniently be performed in a reaction inert solvent such as, for example, 1,4-dioxane, in the presence of a base such as, for example, triethylamine, and optionally in the presence of a catalyst such as, for example, N,N-dimethyl-pyridinamine. Stirring and elevated temperatures may enhance the rate of the reaction.

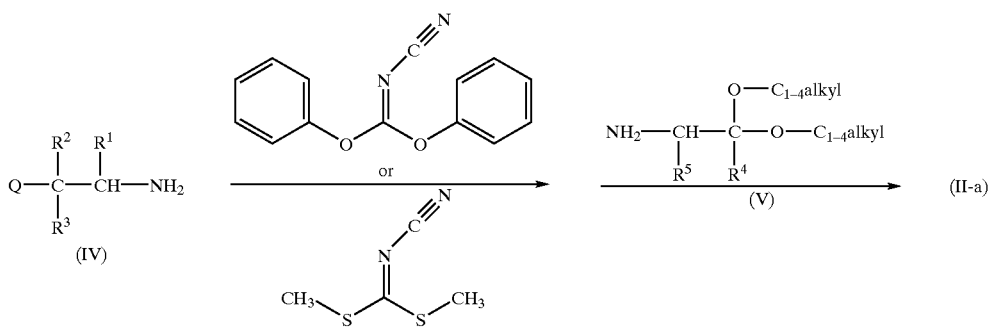

Alternatively, the above reaction may be performed in reverse order, i.e. first react an intermediate of formula (V) with dimethyl cyanocarbonimidodithioate or diphenyl cyanocarbonimidate or a functional derivative thereof, and subsequently react the thus formed intermediate with an amine of formula (IV).

Intermediates of formula (II) wherein D is oxygen, said compounds being represented by formula (II-b), may be prepared by first N-acylating an amine of formula (IV) with phenyl chloroformate or a functional derivative thereof. Said N-acylation can conveniently be performed in a reaction inert solvent such as, for example, dichloromethane, benzene or toluene, optionally cooled on an ice-bath, and in the presence of a base such as, for example, triethylamine or sodiumbicarbonate. The thus obtained intermediate may be subsequently reacted with 2,2-(di$C_{1-4}$alkyloxy) ethanamine (V) or a functional derivative thereof, to form an intermediate of formula (II-b). Said reaction can conveniently be performed in a reaction inert solvent such as, for example, 1,4-dioxane, in the presence of a base such as, for example, triethylamine, and optionally in the presence of a catalyst such as, for example, N,N-dimethyl-pyridin- amine. Stirring and elevated temperatures may enhance the rate of the reaction.

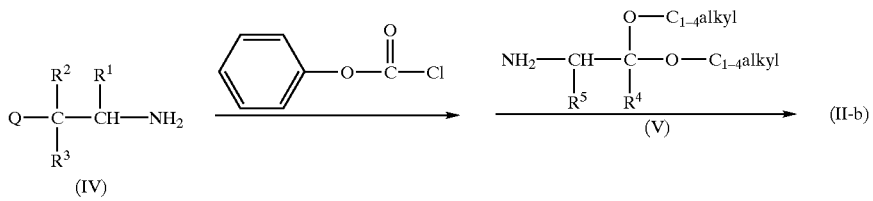

Also, intermediates of formula (II-b) may be directly formed by reacting an intermediate of formula (IV) with a suitable reagent such as, for example, N-[2,2-di-($C_{1-4}$alkyl) ethyl]-1H-imidazole-1-carboxamide or a functional derivative of any one of said reagents.

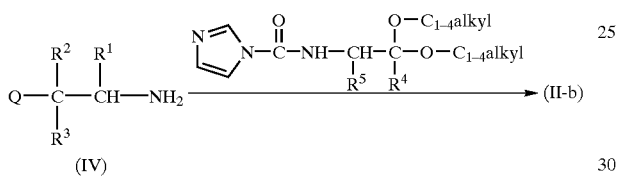

In particular, intermediates of formula (II-b), wherein $R^2$ is a hydroxy group or, preferably, a protected hydroxy group, the protective group P being a trimethylsilyl protecting group or a functional derivative thereof, said intermediates being represented by formula (II-b-1), may be prepared by reacting an intermediate of formula (IV) wherein $R^2$ is a hydroxy group or, preferably, a protected hydroxy group, the protective group P being a trimethylsilyl protecting group or a functional derivative thereof, said intermediates being represented by formula (IV-1), with N-[2,2-di($C_{1-4}$alkyl) ethyl]-1H-imidazole-1-carboxamide or a functional derivative thereof.

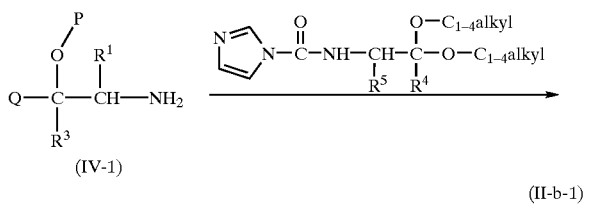

Intermediates of formula (IV) wherein $R^1$ is hydrogen, said intermediates being represented by formula (IV-a), may be prepared by reducing the unsaturated carbon-nitrogen bond in the intermediates of formula (VI) with a suitable reducing agent such as, for example, lithium aluminium hydride or hydrogen in the presence of a catalyst such as, for example, Raney nickel. The cyanide moiety in the intermediates of formula (VI) may also be replaced by a functional derivative thereof such as, for example, an oxime moiety.

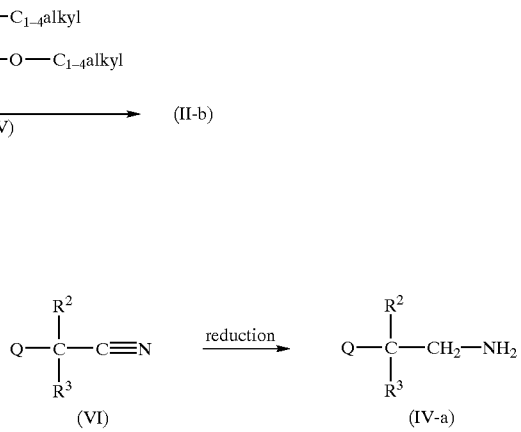

The synthesis of some of the intermediates of formula (VI) is described in WO 95/04045, WO 96/31485, WO 97/03967 and WO 98/14432.

Some of the compounds of formula (I) and some of the intermediates in the present invention contain at least one asymmetric carbon atom. Pure stereochemically isomeric forms of said compounds and said intermediates can be obtained by the application of art-known procedures. For example, diastereomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers.

Pure stereochemically isomeric forms of the compounds of formula (I) may also be obtained from the pure stereochemically isomeric forms of the appropriate intermediates and starting materials, provided that the intervening reactions occur stereo-specifically. The pure and mixed stereochemically isomeric forms of the compounds of formula (I) are intended to be embraced within the scope of the present invention.

An alternative manner of separating the enantiomeric forms of the compounds of formula (I) and intermediates involves liquid chromatography, in particular liquid chromatography using a chiral stationary phase.

The compounds of formula (I), the N-oxide forms, pharmaceutically acceptable acid or base addition salts and the stereochemically isomeric forms thereof, are potent inhibitors of the phosphodiesterase (PDE) isoenzymes of family IV (cAMP-specific family).

cAMP (adenosine cyclic 3',5'-monophosphate) is a key second messenger, the concentration of which affects particular cell activities through activation of enzymes such as kinases. PDE IV is known to hydrolyse cAMP to its corresponding inactive 5'-monophosphate metabolite. Hence, inhibition of PDE IV leads to an elevation of cAMP levels in particular cells such as the respiratory smooth muscle cell and a wide variety of inflammatory cells, i.e. certain lymphocytes, e.g. basophils, neutrophils and eosinophils, monocytes and mast-cells. A number of allergic, atopic and inflammatory diseases are deemed to be caused by higher-than-normal PDE IV concentrations which result in low cAMP levels and hypersensitivity of the thus affected cells for excitatory stimuli. (Examples of said hypersensitivity are for example, excessive histamine release from basophils and mast cells or excessive superoxide anion radical formation by eosinophils.) Hence, the present compounds having potent phosphodiesterase IV inhibitory properties are deemed useful agents in alleviating and/or curing allergic, topic and inflammatory diseases. The functional effects of PDE IV inhibitors are e.g. respiratory smooth muscle relaxation, bronchodilation, platelet aggregation inhibition and inhibition of white blood cell mediator release. Examples of allergic diseases are bronchial asthma, cheilitis, conjunctivitis, contact dermatitis and eczema, irritable bowel disease, deshydroform eczema, urticaria, vasculitis, vulvitis; examples of atopic diseases are dermatitis and eczema, winterfeet, asthma, allergic rhinitis; and related afflictions are, for example, psoriasis and other hyperproliferative diseases.

The compounds of the present invention also have cytokine inhibitory activity. A cytokine is any secreted polypeptide that affects the function of other cells by modulating interactions between cells in the immune or inflammatory response. Examples of cytokines are monokines and lymphokines and they may be produced by a wide variety of cells. For instance, a monokine is generally referred to as being produced and secreted by a mononuclear cell, such as a macrophage and/or monocyte but many other cells produce monokines, such as natural killer cells, fibroblasts, basophils, neutrophils, endothelial cells, brain astrocytes, bone marrow stromal cells, epideral keratinocytes, and 0-lymphocytes. Lymphokines are generally referred to as being produced by lymphocyte cells. Examples of cytokines include Interleukin-1(IL-1), Interleukin-2(IL-2), Interleukin-6(IL-6), Interleukin-8(IL-8), alpha-Tumor Necrosis Factor ($\alpha$TNF) and beta-Tumor Necrosis Factor ($\beta$TNF).

The cytokine specifically desired to be inhibited is $\alpha$TNF. Excessive or unregulated TNF production is implicated in mediating or exacerbating a number of diseases including rheumatoid arthritis, rheumatoid spondylitis, osteoarthritis, gouty arthritis, and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft versus host reaction, allograft rejections, fever and myalgias due to infection, such as influenza, cachexia secondary to infection or malignancy, cachexia secondary to acquired immune deficiency syndrome (AIDS), AIDS, ARC (AIDS related complex), keloid formation, scar tissue formation, Crohn's disease, ulcerative colitis, or pyresis.

The present invention thus also relates to compounds of formula (I) as defined hereinabove, their N-oxides, pharmaceutically acceptable addition salts and stereochemically isomeric forms thereof for use as a medicine, in particular for use as a medicine for treating disease states related to an abnormal enzymatic or catalytic activity of PDE IV, and/or disease states related to a physiologically detrimental excess of cytokines, in particular allergic, atopic and inflammatory diseases, more in particular asthmatic and atopic diseases, most particular atopic dermatitis. Thus the compounds of the present invention may be used for the manufacture of a medicament for treating atopic or asthmatic diseases, more in particular atopic dermatitis.

The present invention also relates to a method of treating warm-blooded animals suffering from disease states related to an abnormal enzymatic or catalytic activity of PDE IV, and/or disease states related to a physiologically detrimental excess of cytokines, in particular allergic, atopic and inflammatory diseases, more in particular asthmatic and atopic diseases, most particular atopic dermatitis. Said method comprises the administration of a therapeutically effective amount of a compound of formula (I) or a N-oxide form, a pharmaceutically acceptable acid or base addition salt or a stereochemically isomeric form thereof in admixture with a pharmaceutical carrier.

In general it is contemplated that an effective daily amount would be from 0.01 mg/kg to 10 mg/kg body weight. It is evident that said effective daily amount may be lowered or increased depending on the response of the treated subject and/or depending on the evaluation of the physician prescribing the compounds of the instant invention. The effective daily amount range mentioned hereinabove are therefore guidelines only and are not intended to limit the scope or use of the invention to any extent.

The PDE IV inhibitory activity of the compounds of formula (I) may be demonstrated in the test "Inhibition of recombinant human mononuclear lymphocyte (MNL) phosphodiesterase type IV B produced in insect cells with a baculovirus vector". Several in vivo and in vitro tests may be used to demonstrate the usefulness of the compounds of formula (I) in treating the described allergic, atopic and inflammatory diseases. Such tests are for instance, "Bronchoconstriction of the guinea pig trachea in vitro", "Bronchoconstriction of the guinea pig trachea in vivo" and the in vivo tests "Arachidonic acid induced pinnal inflammation in mice", "TPA induced ear inflammation in mice", and "Delayed type hypersensitivity in mice".

Further, the present compounds have only very low inhibitory activity on the phosphodiesterase isoenzymes of family III (cGMP-inhibited family). Inhibition of, in particular, PDE III leads to an elevation of cAMP in the cardiac muscle, thereby causing effects on the contractile force of the heart as well as on the relaxation of the heart. In the treatment of the described allergic, atopic and inflammatory diseases, cardiovascular effects clearly are undesired. Hence, as the present compounds inhibit PDE IV at much lower concentrations as they inhibit PDE III, their therapeutic use may be adjusted to avoid cardiovascular side-effects.

Art-known PDE IV inhibitors often cause adverse gastro-intestinal side effects. Most of the present compounds, however, have few effects on the gastro-intestinal tract, which may be demonstrated in the test "Gastric emptying of a caloric meal in rats".

The designation PDE III and IV as used herein refers to the classification by J. A. Beavo and D. H. Reifsnyder, TIPS Reviews, Apr. 1990. pp. 150–155.

The cytokine inhibitory activity of the compounds of formula (I), such as the inhibition of $\alpha$TNF production, may be demonstrated in the in vitro test "Cytokine production in human whole blood cultures".

In addition, the compounds of the present invention are expected to show no or little endocrinological side-effects. This may be evidenced by, for instance, the "Testosterone in vivo" test, the "In vitro inhibition of the aromatase activity"-test and the "In vivo inhibition of the aromatase activity"-test.

In view of their useful PDE IV and cytokine inhibiting properties, the subject compounds may be formulated into various pharmaceutical compositions for administration purposes comprising a pharmaceutically acceptable carrier, and as active ingredient a therapeutically effective amount of a compound of formula (I). To prepare the pharmaceutical compositions of this invention, a therapeutically effective amount of the particular compound, in base or acid addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, rectally, topically, percutaneously, by inhalation or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral unit dosage form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment or cream. As appropriate compositions for topical application there may be cited all compositions usually employed for topically administering drugs e.g. creams, gellies, dressings, shampoos, tinctures, pastes, lotions, solutions, ointments, salves, powders and the like. Application of said compositions may be by aerosol, e.g. with a propellant such as nitrogen, carbon dioxide, a freon, or without a propellant such as a pump spray, drops, lotions, or a semisolid such as a thickened composition which can be applied by a swab. In particular, semisolid compositions such as salves, creams, gellies, ointments and the like will conveniently be used.

In order to enhance the solubility and/or the stability of the compounds of formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin. Also co-solvents such as alcohols may improve the solubility and/or the stability of the compounds of formula (I) in pharmaceutical compositions. In the preparation of aqueous compositions, addition salts of the subject compounds are obviously more suitable due to their increased water solubility.

It is especially advantageous to formulate the aforementioned pharmaceutical compositions in unit dosage form for ease of administration and uniformity of dosage. Unit dosage form refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

The following examples are intended to illustrate the scope of the present invention.

Experimental part

Hereinafter, "THF" means tetrahydrofuran, "RT" means room temperature, "DMF" means N,N-dimethylformamide, "EtOAc" means ethylacetate and "DIPE" means diisopropylether.

A. Preparation of the intermediate compounds

EXAMPLE A1 a) A mixture of (±)-6-(2-amino-1-methylethyl)4-(cyclopentyloxy)-3-pyridinol (0.037 mol) and $NaHCO_3$ (0.0814 mol) in $CH_2Cl_2$ (200 ml) was stirred at 0–5° C. A solution of phenyl carbonochloridate (0.074 mol) in $CH_2Cl_2$ (50 ml) was added dropwise and the resulting reaction mixture was stirred for one hour at RT. The reaction mixture was poured out into water and the layers were separated. The aqueous phase was extracted twice with $CH_2Cl_2$. The combined organic layers were dried, filtered and the solvent evaporated, yielding 18.2 g (±)-phenyl [2-[4-(cyclopentyloxy)-5-[(phenoxycarbonyl) oxy]-2-pyridinyl] propyl]carbamate (interm. 1).

b) A mixture of intermediate (1) (0.037 mol), 2,2-dimethoxyethanamine (0.148 mol), triethylamine (0.148 mol) and 4-dimethylaminopyridine (catalytic quantity) in 1,4-dioxane (150 ml) was stirred and refluxed for 60 hours. The solvent was evaporated. The residue was purified by column chromatography over silica gel (eluent: $CH_2Cl_2$/ $CH_3OH$ 95/5 and $CH_2Cl_2$/($CH_3OH/NHO_3$) 95/5). The pure fractions were collected and the solvent was evaporated, yielding 13g (95.6%) of (±)-N-[2-[4-(cyclopentyloxy)-5-hydroxy-2-pyridinyl]propyl]-N'-(2,2-dimethoxyethyl)urea (interm. 2).

EXAMPLE A2 a) A mixture of 4-(cyclopentyloxy)-5-methoxy-2-pyridineethanamine (0.026 mol) and triethylamine (0.03 mol) in $CH_2Cl_2$ (75ml) was stirred at 0–5° C. A mixture of phenyl carbonochloridate (0.03 mol) in $CH_2Cl_2$ (25ml) was added dropwise. The mixture was stirred at RT for 1 hour and then washed with NaOH (1N) and water. The organic layer was separated, dried, filtered and the solvent was evaporated. The residue was purified over silica gel on a glass filter (eluent: $CH_2Cl_2/CH_3OH$ 98/2). The pure fractions were collected and the solvent was evaporated. The residue was dried, yielding 7.2g (77.7%) of phenyl [2-[4-(cyclopentyloxy)-5-methoxy-2-pyridinyl]ethyl]carbamate (interm. 3).

b) A mixture of intermediate (3) (0.018 mol), 2,2-dimethoxyethanamine (0.02 mol), 4-dimethylaminopyridine (0.005 mol) and triethylamine (0.036 mol) in 1,4-dioxane (75 ml) was stirred and refluxed for 48 hours. The solvent was evaporated. The residue was dissolved in $CH_2Cl_2$ and washed with NaOH 1N and water. The organic layer was separated, dried, filtered and the solvent was evaporated, yielding 6.6 g (100%) of N-[2-[4-(cyclopentyloxy)-5-methoxy-2-pyridinyl]ethyl]-N'-(2,2-dimethoxyethyl)urea (interm. 4).

EXAMPLE A3 a) A mixture of 1,1'-carbonylbis[1H-imidazole] (2 mol) in EtOAc (800 ml) was stirred and cooled on an ice-bath, resulting in a suspension. 2,2-dimethoxyethanamine (2 mol) was added dropwise while the temperature was kept below 25° C. The resulting reaction mixture was stirred for 2 hours at RT, then for 30 minutes while cooling on an ice-bath. The precipitate was filtered off, stirred in EtOAc (400 ml) during 15 minutes, and on an ice-bath during 15 minutes. The precipitate was filtered off, washed with DIPE (2×50 ml), and dried, yielding 277 g (70%) of N-(2,2-dimethoxyethyl)-1H-imidazole-1-carboxamide (interm. 5).

b) A mixture of (±)4-(cyclopropylmethoxy)-5-methoxy-β-methyl-2-pyridineethanamine (0.025 mol) and intermediate (5) (0.025 mol) in THF (100 ml) was stirred and refluxed for 2 hours. The solvent was evaporated. The residue was stirred in water and this mixture was extracted with toluene and EtOAc. The separated organic layer was dried, filtered, and the solvent evaporated, yielding 9.1 g (100%) of (±)-N-[2-[4-(cyclopropylmethoxy)-5-methoxy-2-pyridineyl] propyl]—N'-(2,2-dimethoxyethyl)urea (interm. 6).

EXAMPLE A4 a) A mixture of 5-methoxy-4-[(tetrahydro-3-furanyl)oxy]-2-pyridinecarboxaldehyde (0.057 mol) and $ZnI_2$ (0.0027 mol) in $CH_2Cl_2$ (130 ml) was stirred at RT. Trimethyl silanecarbonitrile (0.0684 mol) in $CH_2Cl_2$ (30 ml) was added dropwise. The resulting reaction mixture was stirred for 90 minutes at RT. Water was added and the mixture was stirred for 10 minutes (2x). The separated organic layer was dried, filtered and the solvent was evaporated. Toluene was added and azeotroped on the rotary evaporator, yielding (±)-5-methoxy-4-[(tetrahydro-3-furanyl)oxy]-α-[(trimethylsilyl) oxy]-2-pyridineacetonitrile (quantitative yield) (interm. 7).

b) A mixture of intermediate (7) (0.074 mol) in THF (500 ml) was hydrogenated with Raney nickel (3 g) as a catalyst. After uptake of $H_2$ (2 equivalents), the catalyst was filtered off and the filtrate was evaporated, yielding (±)-5-methoxy-4-[(tetrahydro-3-furanyl)oxy]-β-[(trimethylsilyl)oxy]-2-pyridineethanamine(quantitative yield) (interm. 8).

EXAMPLE A5 a) A solution of (±)-6-(cyclopentyloxy)-5-methoxy-β-methyl-2-pyridineethanamine (0.037 mol) and diphenyl N-cyanocarbonimidate (0.037 mol) in ethanol (100 ml) was stirred for one day at RT. The precipitate was filtered off, washed with ethanol, DIPE, then dried, yielding 9 g (61.7%) of (±)-phenyl N'-cyano-N-[2-[6-(cyclopentyloxy)-5-methoxy-2-pyridinyl]propyl]carbamimidate(interm. 9). The filtrate was evaporated under reduced pressure. The residue was dissolved in $CH_2Cl_2$. The organic solution was washed three times with 2 N NaOH. The organic layer was separated, dried, filtered and the solvent was evaporated, yielding 4.1 g of intermediate (9). Total yield is 89%.

b) A mixture of 2,2-dimethoxyethanamine (0.015 mol), triethylamine (0.026 mol) and 4-dimethylaminopyridine (0.0065 mol) in 1,4-dioxane (50 ml) was added to a solution of intermediate (9) (0.013 mol) in 1,4-dioxane (50 ml). The resulting reaction mixture was stirred and refluxed overnight. The solvent was evaporated. The residue was taken up into water and this mixture was extracted with $CH_2Cl_2$. The separated organic layer was dried, filtered and the solvent evaporated. The residue was purified by column chromatography over silica gel (eluent: $CH_2Cl_2/CH_3OH$ 99/1). The pure fractions were collected and the solvent was evaporated, yielding 4.13 g (79%) of (±)-N"-cyano-N-[2-[6-(cyclopentyloxy)-5-methoxy-2-pyridinyl]propyl]—N'-(2,2-dimethoxyethyl)guanidine (interm. 10).

EXAMPLE A6

Reaction under $N_2$. A solution of ethanediol dichloride (0.0210 mol) in $CH_2Cl_2$ (40 ml) was stirred at −60° C. A solution of dimethyl sulfoxide (0.0420 mol) in $CH_2Cl_2$ (10 ml) was added dropwise and stirring was continued for 5 min at −60° C. A solution of 1,3-dihydro-1-[2-hydroxy-2-[5-methoxy-4-[(5-phenylpentyl)oxy]-2-pyridinyl]ethyl]-2H-imidazol-2-one (compound 18) (0.0070 mol) in $CH_2Cl_2$ (10 ml) was added dropwise at −60° C. and stirring was continued for 15 min at −60° C. Triethylamine (0.0770 mol) was added dropwise at −60° C. and stirring was continued for 5 min. The mixture was treated with water, then extracted with $CH_2Cl_2$. The separated organic layer was dried ($MgSO_4$), filtered, and the solvent was evaporated. The residue was purified by column chromatography over silica gel (eluent: $CH_2Cl_2/CH_3OH$ 94/6). The pure fractions were collected and the solvent was evaporated, yielding 1.8 g (69.6%) of 1,3-dihydro-1-[2-[5-methoxy-4-[(5-phenylpentyl)oxy]-2-pyridinyl]-2-oxoethyl]-2H-imidazol-2-one (interm. 11).

Preparation of the compounds of formula (I)

EXAMPLE B1

A mixture of intermediate (2) (0.037 mol) and HCl 1N (0.1 mol) in methanol (300 ml) was stirred for 5 days at RT. The mixture was basified with $NH_3/CH_3OH$. The solvent was evaporated and the residue was purified by column chromatography over silica gel (eluent: $CH_2Cl_2/CH_3OH$ 95/5). The pure fractions were collected and the solvent was evaporated. The residue was stirred in DIPE, filtered off, then dried, yielding 5.9 g (52.7%) of (±)-1-[2-[4-(cyclopentyloxy)-5-hydroxy-2-pynidinyl]propyl]-1,3-dihydro-2H-imidazol-2-one (compound 1).

EXAMPLE B2

A mixture of compound (1) (0.0194 mol), chloro difluoromethyl and $K_2CO_3$ (0.0194 mol) in methanol (100 ml) was stirred for 16 hours at 125° C. in an autoclave. The solvent was evaporated. The residue was purified by column chromatography over silica gel (eluent: $CH_2Cl_2/CH_3OH$ 95/5, upgrading to 80/20). The pure fractions were collected and the solvent was evaporated. The residue was dissolved in 2-propanone and converted into the hydrochloric acid salt (1:2) with HCl/2-propanol. The precipitate was filtered off and dried, yielding 0.58 g (7%) of (±)-1-[2-[4-(cyclopentyloxy)-5-[(difluoromethyl)oxy]-2-pyridinyl]-propyl]-1,3-dihydro-2H-imidazol-2-one.2HCl (compound 20).

EXAMPLE B3

HCl 0.5M (30.3 ml) was added dropwise to a solution of intermediate (10) (0.0101 mol) in THF (82 ml) and the resulting reaction mixture was stirred and refluxed for 2 hours. The reaction mixture was cooled, treated with water, alkalized with $Na_2CO_3$ and this mixture was extracted with EtOAc. The separated organic layer was dried, filtered and the solvent evaporated. The residue was purified by column chromatography over silica gel (eluent: CH$_2$Cl$_2$/CH$_3$OH 90/10). The desired fractions were collected and the solvent was evaporated. The residue was repurified by column chromatography over silica gel (eluent: CH$_2$Cl$_2$/CH$_3$OH 100/0, upgrading to 95/5). The pure fractions were collected and the solvent was evaporated. The residue was stirred in DIPE, filtered off, and dried. The obtained product was repurified by high-performance liquid chromatography. The pure fractions were collected and the solvent was evaporated. The residue was stirred in DIPE, filtered off, washed and dried, yielding 0.54g (±)-[1-[2-[6-(cyclopentyloxy)-5-methoxy-2-pyridinyl]propyl]-1,3-dihydro-2H-imidazol-2-ylidene]cyanamide (compound 22).

EXAMPLE B4

Reaction under N$_2$ flow. A solution of intermediate (11) (0.0049 mol) in THF (50 ml) was stirred at 0–5° C. CH$_3$MgCl (0.0054 mol) was added dropwise. The reaction mixture was decomposed with a saturated aqueous NH$_4$Cl solution, then extracted with CH$_2$Cl$_2$. The separated organic layer was dried, filtered, and the solvent was evaporated. The residue was purified by column chromatography over silica gel (eluent: CH$_2$Cl$_2$/CH$_3$ OH 95/5). The desired fractions were collected and the solvent was evaporated. The residue (0.5 g) was repurified by high-performance liquid chromatography (eluent: CH$_2$Cl$_2$/CH$_3$OH 98/2, upgrading to 90/10). The pure fractions were collected and the solvent was evaporated. The residue was stirred in DIPE, filtered off, washed, then dried, yielding 0.20 g (±)-1,3-dihydro-1-[2-hydroxy-2-[5-methoxy-4-[(5-phenylpentyl)oxy]-2-pyridinyl]propyl]-2H-imidazol-2-one (compound 23).

The following compounds were prepared according to one of the above examples (Ex. No.).

TABLE 1

| Co. No. | Ex. no. | R$^2$ | R$^3$ | R$^7$ | R$^8$ | Salt |
|---|---|---|---|---|---|---|
| 1 | B.1 | CH$_3$ | H | cyclopentyl | H | |
| 2 | B.1 | CH$_3$ | H | 3-tetrahydrofuranyl | H | |
| 3 | B.1 | H | H | cyclopentyl | CH$_3$ | |
| 4 | B.1 | CH$_3$ | H | cyclopentyl | CH$_3$ | HCl (1:1) hydrate (1:1) |
| 5 | B.1 | H | H | cyclopropylmethyl | CH$_3$ | |
| 6 | B.1 | CH$_3$ | H | cyclopropylmethyl | CH$_3$ | |
| 7 | B.1 | CH$_3$ | CH$_3$ | cyclopentyl | CH$_3$ | |
| 9 | B.1 | CH$_3$ | H | 3-tetrahydrofuranyl | CH$_3$ | |
| 10 | B.1 | CH$_3$ | H | phenylpentyl | CH$_3$ | HCl (1:1) |
| 15 | B.1 | OH | H | 3-tetrahydrofuranyl | CH$_3$ | |
| 16 | B.1 | OH | H | 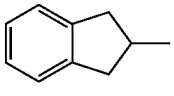 | CH$_3$ | |
| 17 | B.1 | OH | H | cyclopropylmethyl | CH$_3$ | |
| 18 | B.1 | OH | H | phenylpentyl | CH$_3$ | |
| 19 | B.1 | OH | H | cyclopentyl | CH$_3$ | |
| 20 | B.2 | CH$_3$ | H | cyclopentyl | CHF$_2$ | HCl (1:2) |
| 21 | B.2 | CH$_3$ | H | 3-tetrahydrofuranyl | CHF$_2$ | HCl (1:2) |
| 23 | B.4 | OH | CH$_3$ | phenylpentyl | CH$_3$ | |

TABLE 2

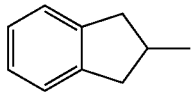

| Co. No. | Ex. no. | R$^2$ | R$^3$ | R$^7$ | R$^8$ |
|---|---|---|---|---|---|
| 11 | B.1 | H | H | cyclopentyl | CH$_3$ |
| 12 | B.1 | CH$_3$ | H | cyclopentyl | CH$_3$ |

TABLE 3

| Co. No. | Ex. no. | R$^2$ | R$^3$ | R$^7$ | R$^8$ | D |
|---|---|---|---|---|---|---|
| 8 | B.1 | CH$_3$ | H | (indanyl structure) | CH$_3$ | O |
| 13 | B.1 | H | H | cyclopentyl | CH$_3$ | O |
| 14 | B.1 | CH$_3$ | H | cyclopentyl | CH$_3$ | O |
| 22 | B.4 | CH$_3$ | H | cyclopentyl | CH$_3$ | N—CN |

Table 4 lists both the experimental (column heading "Exper") and theoretical (column heading "Theor") elemental analysis values for carbon (C), hydrogen (H) and nitrogen (N) for the compounds as prepared in the experimental part hereinabove.

TABLE 4

| Co. No. | C Theor | C Exper | H Theor | H Exper | N Theor | N Exper |
|---|---|---|---|---|---|---|
| 3 | 61.84 | 63.35 | 7.08 | 6.98 | 13.46 | 13.85 |
| 4 | 54.77 | 54.91 | 7.17 | 7.05 | 11.21 | 11.3 |
| 5 | 62.05 | 62.27 | 6.76 | 6.62 | 14.39 | 14.52 |
| 6 | 63.28 | 63.35 | 7.05 | 6.98 | 13.74 | 13.85 |
| 7 | 65.08 | 65.23 | 7.73 | 7.6 | 12.71 | 12.68 |
| 8 | 69.04 | 69.02 | 6.6 | 6.34 | 11.71 | 11.5 |
| 9 | 60.06 | 60.18 | 6.88 | 6.63 | 13.24 | 13.16 |
| 11 | 63.47 | 63.35 | 6.78 | 6.98 | 13.88 | 13.85 |
| 12 | 64.29 | 64.33 | 7.51 | 7.3 | 13.21 | 13.24 |
| 13 | 63.41 | 63.35 | 6.91 | 6.98 | 13.73 | 13.85 |
| 14 | 64.25 | 64.33 | 7.34 | 7.3 | 13.23 | 13.24 |
| 15 | 56.56 | 56.07 | 6.15 | 5.96 | 13.48 | 13.08 |
| 16 | 64.86 | 65.38 | 5.8 | 5.76 | 11.17 | 11.44 |
| 17 | 58.92 | 59.01 | 6.33 | 6.27 | 14.13 | 13.76 |
| 18 | 66.32 | 66.48 | 7 | 6.85 | 10.69 | 10.57 |
| 19 | 59.65 | 60.18 | 6.51 | 6.63 | 13.1 | 13.16 |
| 20 | 47.78 | 47.9 | 5.25 | 5.44 | 9.75 | 9.86 |
| 21 | 44.73 | 44.87 | 4.67 | 4.94 | 9.66 | 9.81 |

TABLE 4-continued

| Co. No. | C Theor | C Exper | H Theor | H Exper | N Theor | N Exper |
|---|---|---|---|---|---|---|
| 22 | 63.25 | 63.32 | 6.86 | 6.79 | 20.77 | 20.51 |
| 23 | 66.11 | 67.13 | 6.95 | 7.1 | 9.97 | 10.21 |

C. Pharmacological example

EXAMPLE C.1

Inhibition of Recombinant Human Mononuclear Lymphocyte (MNL) Phosphodiesterase Type IV B Produced in Insect Cells with a Baculovirus Vector The alleviating and/or curing effect of the instant compounds on allergic and atopic diseases was assessed by an in vitro assay system to detect an inhibiting effect on the recombinant human MNL phosphodiesterase type IV B.

Seventy-two hours after infection with recombinant baculovirus, the insect cells were harvested and pelleted at 500 g for 5 minutes. The cells were lysed in 10 ml lysis-buffer consisting of 20 mM Tris, 10 mM EGTA, 2 mM $Na_2EDTA$, 1% Triton-X-100, 1 mM $Na_3VO_4$, 10 mM NaF, 2 µg/ml of leupeptine, pepstatine and aprotinine, 0.3 µg/ml benzamidine and 100 µg/ml TPCK pH 7.5. After 5 minutes on ice, solubilized cells were centrifuged at 4000 rpm for 15 minutes at 4° C. The resulting supernatant was filtered through a 0.45 µm filter (Millipore) and brought to TBS buffer (50 mM Tris, 150 mM NaCl pH 7.4).

The supernatant containing phosphodiesterase (PDE) type IV B, was subsequently loaded onto a 5 ml anti-FLAG-$M_2$ affinity gel column, previously activated with 5 ml 100 mM glycine pH 3.5 and equilibrated with 20 ml 50 mM Tris, 150 mM NaCl pH 7.4. After washing the column with equilibration buffer, PDE IV was eluted in 1.5 ml fractions containing 37.5 µl IM Tris pH 8. The fractions were dialyzed overnight against 20 mM Tris, 2mM $Na_2EDTA$ and 400 mM NaCl pH 7.5 and tested for PDE IV activity. Identification was done on SDS PAGE and Western Blot (anti-FLAG-$M_2$). Active fractions were pooled, brought to 10% glycerol and stored at −70° C.

The incubation mixture (pH 8) (200 µl) contained 20 mM Tris, 10 mM magnesium sulphate, 0.8 µM $^3$H-cAMP (310 mCi/mmole) and the phosphodiesterase type IV, the amount depending on the enzymatic activity. A protein concentration was chosen that showed a linear increase of phosphodiesterase activity during an incubation period of maximum 10 minutes at 37° C. and where less than 10% of the initial substrate was hydrolyzed.

When the effect of different compounds on phosphodiesterase activity was tested, the medium without cAMP was incubated with the compound(s) or its carrier (DMSO—1% final concentration) for 5 minutes. The enzymatic reaction was started by addition of $^3$H-cAMP and stopped 10 minutes later after transferring the microtiter-plate in a waterbath at 100° C. for 5 minutes. After cooling to RT, alkaline phosphatase (0.25 µg/ml) was added and the mixture was incubated at 37° C. for 20 minutes. 100 µl of the mixture was subsequently applied to a GF-B filter-microtiter-plate (Millipore) filled with 300 µl DEAE-Sephadex-A25 suspension. The plate was washed 3 times with 75 µl 20 mM Tris pH 7.5 and the filtrates were collected for counting in the Packard Top Count scintillation counter.

The inhibiting effect of the present compounds on recombinant human MNL phosphodiesterase PDE IV B was measured at different concentrations of the instant compounds. The % activity of PDE IV B versus control was calculated and listed in Table 5.

TABLE 5

| Co. No. | Test Dose | % Activity |
|---|---|---|
| 3 | $10^{-6}$ M | 56 |
| 4 | $10^{-7}$ M | 60 |
| 5 | $10^{-6}$ M | 57 |
| 6 | $10^{-7}$ M | 72.5 |
| 7 | $10^{-7}$ M | 78 |
| 8 | $10^{-7}$ M | 68.5 |
| 9 | $10^{-7}$ M | 68 |
| 10 | $10^{-6}$ M | 57 |
| 11 | $10^{-7}$ M | 75 |
| 12 | $10^{-7}$ M | 59 |
| 13 | $10^{-7}$ M | 49 |
| 14 | $10^{-7}$ M | 18 |
| 15 | $10^{-6}$ M | 88 |
| 16 | $10^{-6}$ M | 63 |
| 17 | $10^{-7}$ M | 75 |
| 18 | $10^{-6}$ M | 77 |
| 19 | $10^{-6}$ M | 60.5 |
| 21 | $10^{-6}$ M | 73 |
| 22 | $10^{-7}$ M | 25 |
| 23 | $10^{-6}$ M | 35 |

Composition examples

The following formulations exemplify typical pharmaceutical compositions suitable for systemic or topical administration to animal and human subjects in accordance with the present invention.

"Active ingredient" (A.I.) as used throughout these examples relates to a compound of formula (I), or a N-oxide form, a pharmaceutically acceptable addition salt or a stereochemically isomeric form thereof.

Example D.1

Film-coated Tablets

Preparation of Tablet Core

A mixture of 100 g of the A.I., 570 g lactose and 200 g starch was mixed well and thereafter humidified with a solution of 5 g sodium dodecyl sulfate and 10 g polyvinylpyrrolidone in about 200 ml of water. The wet powder mixture was sieved, dried and sieved again. Then there was added 100 g microcrystalline cellulose and 15 g hydrogenated vegetable oil. The whole was mixed well and compressed into tablets, giving 10.000 tablets, each comprising 10 mg of the active ingredient.

Coating

To a solution of 10 g methyl cellulose in 75 ml of denaturated ethanol there was added a solution of 5 g of ethyl cellulose in 150 ml of dichloromethane. Then there were added 75 ml of dichloromethane and 2.5 ml 1,2,3-propanetriol. 10 g of polyethylene glycol was molten and dissolved in 75 ml of dichloromethane. The latter solution was added to the former and then there were added 2.5 g of magnesium octadecanoate, 5 g of polyvinylpyrrolidone and 30 ml of concentrated color suspension and the whole was homogenated. The tablet cores were coated with the thus obtained mixture in a coating apparatus.

EXAMPLE D.2

2% Topical Cream

To a solution of 200 mg hydroxypropyl β-cyclodextrine in purified water is added 20 mg of A.I. while stirring. Hydrochloric acid is added until complete dissolution and next sodium hydroxide is added until pH 6.0. While stirring, 50 mg glycerol and 35 mg polysorbate 60 are added and the mixture is heated to 70° C. The resulting mixture is added to a mixture of 100 mg mineral oil, 20 mg stearyl alcohol, 20 mg cetyl alcohol, mg glycerol monostearate and 15 mg sorbate 60 having a temperature of 70° C. while mixing slowly. After cooling down to below 25° C., the rest of the purified water q.s. ad 1 g is added and the mixture is mixed to homogenous.

What is claimed is:

1. A compound having the formula

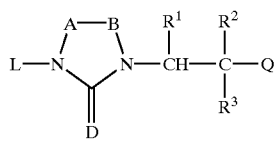

(I)

wherein:

L is hydrogen; $C_{1-6}$alkyl; $C_{1-6}$alkyl substituted with one or two substituents selected from the group consisting of hydroxy, $C_{1-4}$alkyloxy, $C_{1-4}$alkyloxycarbonyl, mono- and di($C_{1-4}$alkyl)amino, aryl and Het$^2$; $C_{3-6}$alkenyl; $C_{3-6}$alkenyl substituted with aryl; $C_{1-6}$alkylcarbonyl; $C_{1-6}$alkyloxycarbonyl; piperidyl; piperidyl substituted with $C_{1-4}$alkyl or aryl$C_{1-4}$alkyl; $C_{1-6}$alkylsulfonyl or arylsulfonyl;

—A—B— is a bivalent radical of formula:

—CR$^4$=CR$^5$—  (a-1); or

—CHR$^4$—CHR$^5$—  (a-2);

D is O or NR$^6$;

Q is a radical of the formula (b-1)

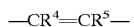

(b-2)

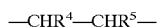

(b-3)

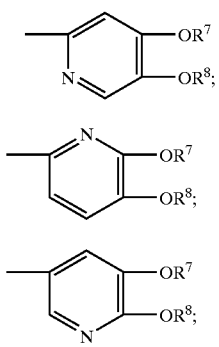

$R^1$ is hydrogen or $C_{1-4}$alkyl;

or $R^1$ and $R^2$ together may form a bivalent radical of formula —(CH$_2$)$_m$— wherein m is 1, 2, 3 or 4;

$R^2$ and $R^3$ are each independently hydrogen; $C_{1-6}$alkyl; or hydroxy;

$R^4$ and $R^5$ are each independently selected from hydrogen or $C_{1-4}$alkyl;

$R^6$ is hydrogen, $C_{1-4}$alkyl or cyano;

$R^7$ and $R^8$ each independently are hydrogen; $C_{1-6}$alkyl; difluoromethyl; $C_{3-6}$cycloalkyl; tetrahydrofuranyl; indanyl; or $C_{1-10}$alkyl substituted with aryl, indanyl, 6,7-dihydro-5H-cyclopentapyridyl, or $C_{3-6}$cycloalkyl;

aryl is phenyl or phenyl substituted with one, two or three substituents each independently selected from halo, hydroxy, $C_{1-4}$alkyl, $C_{1-4}$alkyloxy, $C_{3-6}$cycloalkyl, trifluoromethyl, amino, nitro, carboxyl, $C_{1-4}$alkyloxycarbonyl and $C_{1-4}$alkylcarbonylamino;

Het$^2$ is morpholinyl; piperidyl; piperidyl substituted with $C_{1-4}$alky or aryl$C_{1-4}$alky; piperazinyl; piperazinyl substituted with $C_{1-4}$alkyl or aryl$C_{1-4}$alkyl; pyridyl; pyridyl substituted with $C_{1-4}$alkyl; furanyl; furanyl substituted with $C_{1-4}$alkyl; thienyl or thienyl substituted with $C_{1-4}$alkyl or $C_{1-4}$alkylcarbonylamino;

and the pharmaceutically acceptable acid or base addition salt forms or stereochemically isomeric forms thereof.

2. A compound according to claim 1 wherein $R^7$ and $R^8$ are each independently $C_{1-6}$alkyl; $C_{3-6}$cycloalkyl; difluoromethyl; tetrahydrofuranyl; indanyl; or $C_{1-10}$alkyl substituted with aryl, indanyl, 6,7-dihydro-5H-cyclopentapyridyl or $C_{3-6}$cycloalkyl.

3. A compound according to claim 1 wherein $R^7$ is cyclopentyl, tetrahydrofuranyl, cyclopropylmethyl, 5-phenylpentyl or indanyl; $R^8$ is hydrogen, methyl or difluoromethyl; $R^2$ is hydrogen or methyl; $R^3$ is hydrogen, hydroxy or methyl and $R^1$, $R^4$, $R^5$ and L are hydrogen.

4. A compound according to claim 1 wherein the compound is:

[1-[2-[6-(cyclopentyloxy)-5-methoxy-2-pynddiny]propyl]-1,3-dihydro-2H-imidazol-2-ylidene]cyanamide; and [1-[2-[6-(cyclopentyloxy)-5-methoxy-2-pyridinyl]propyl]-1,3-dihydro-2H-imidazol-2-one, or a stereochemically isomeric form or a pharmaceutically acceptable acid or base addition salt thereof.

5. A composition comprising a pharmaceutically acceptable carrier, and as active ingredient a therapeutically effective amount of a compound as claimed in 1.

6. A process of preparing a composition comprising mixing a pharmaceutically acceptable carrier with a therapeutically effective amount of a compound as claimed in claim 1.

7. A method for treating atopic or asthmatic diseases in a warm-blooded animal in need thereof comprising administering to the warm-blooded animal a therapeutically effective amount of the compound of claim 1.

8. A process of preparing a compound as claimed in claim 1, said process comprising:

a) cyclization of an intermediate of formula (II) wherein $R^1$ to $R^5$, D and Q are defined as in claim 1,

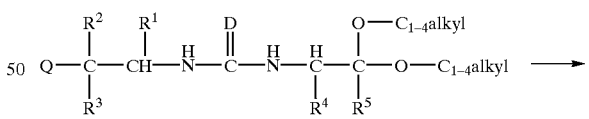

(II)

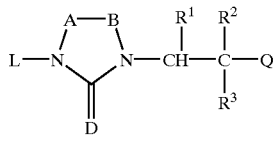

(I-a-1)

in a reaction inert solvent and in the presence of a suitable acid; thus forming a compound of formula (I-a-1);

b) cyclization of an intermediate of formula (II-1) wherein $R^1$ to $R^5$, D and Q are defined as in claim 1 and P is hydrogen or a trimethylsilyl protecting group

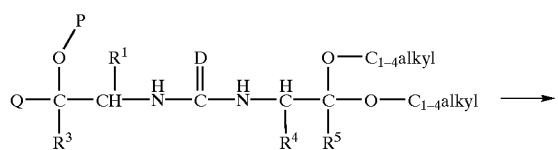

(II-1)

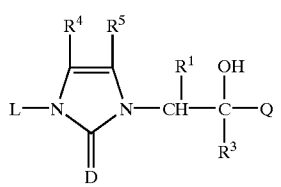

(I-a-1-1)

in a reaction inert solvent and in the presence of a suitable acid; thus forming a compound of formula (I-a-1-1).

9. The process of claim 8, further comprising either:
   (1) converting the compound of formula (I) into a therapeutically active non-toxic acid addition salt by treatment with an acid or a therapeutically active non-toxic base addition salt by treatment with a base;
   (2) converting the acid addition salt form into the free base by treatment with alkali; or
   (3) converting the base addition salt into the free acid by treatment with acid.

10. The process of claim 9, further comprising preparing a stereochemically isomeric form of the compound of claim 1 of the salt thereof.

* * * * *